United States Patent [19]
Dunning et al.

[11] Patent Number: 6,023,003
[45] Date of Patent: Feb. 8, 2000

[54] PROCESS AND SYSTEM FOR RECOVERING GLYCOL FROM GLYCOL/BRINE STREAMS

[75] Inventors: Timothy R. Dunning, The Woodlands, Tex.; Ralph L. Hicks, New Orleans, La.; Rita W. Girau, Harvey, La.; Kiel M. Divens, New Orleans, La.; Richard I. Evans, Baton Rouge, La.

[73] Assignee: Reading & Bates Development Co., Houston, Tex.

[21] Appl. No.: 09/006,229

[22] Filed: Jan. 13, 1998

[51] Int. Cl.[7] .................................................. C07C 27/26
[52] U.S. Cl. ........................... 568/868; 568/862; 568/858
[58] Field of Search .................................. 568/862, 868, 568/858

[56] References Cited

U.S. PATENT DOCUMENTS

| | | | |
|---|---|---|---|
| 3,726,929 | 4/1973 | Payne et al. | 568/778 |
| 3,789,065 | 1/1974 | Kollar | 210/497 |
| 4,200,765 | 4/1980 | Goetz | 568/862 |
| 4,427,507 | 1/1984 | Aken et al. | 204/522 |
| 4,460,383 | 7/1984 | Valerius . | |
| 4,687,546 | 8/1987 | Willis . | |
| 4,810,340 | 3/1989 | Blytas et al. | 204/525 |
| 5,234,552 | 8/1993 | McGraw et al. . | |

FOREIGN PATENT DOCUMENTS

| | | |
|---|---|---|
| 0 168 893 | 1/1986 | European Pat. Off. . |
| 2084885 | 4/1982 | United Kingdom . |
| WO 94/22546 | 10/1994 | WIPO . |

OTHER PUBLICATIONS

Hydrate Prevention With Gas Expansion, Subsurface Heat, J.L. Beauquin & J.C. Fechant, Offshore, Aug. 1997, pp. 104–106.

Operations & Maintenance Manual, Vortoil Separation Systems; Vortoil K–Liner Separator, Document No. 6803, Rev. 2, Aug. 1995, pp. 1–15.

Separators Versus Hydrocyclones, Two Different Solutions to Solids/Liquid Separation; Reprinted from Filtration News, Jan./Feb. 1989.

Simulation and Control of a Multiple Effect Evaporator; K.M. Nielsen & T.S. Pedersen & F.D. Nielsen, Aalborg University, Department of Control Engineering, Institute for Electronic Systems, Denmark.

A Shortcut for Designing Evaporators; A Simple and Fast Method for Finding the Optimum Number of Effects; M.I. Alejandro Anaya Durand, Instituto Mexicano del Petroleo, Chemical Engineering/Jan. 1996, pp. 123–126.

Survey of Solar Desalination Systems and System Selection, Soteris Kalogirou, Dept. of Mechanical Engineering, Higher Technical Institute, Nicosia, Cyprus, pp. 69–81.

Performance Assessment of Multistage Absorption Cycles, K. Cheung, Y. Hwang, J.F. Judge, K. Kolos, A. Singh and R. Radermacher, Dept. of Mechanical Engineering, College Park, MD, pp. 472–481.

*Primary Examiner*—James O. Wilson
*Attorney, Agent, or Firm*—Akin, Gump, Strauss, Hauer & Feld, L.L.P.

[57] ABSTRACT

A process and a system is disclosed for recovering glycol from glycol and brine mixtures produced from oil or natural gas wells that combines energy efficiency with a capability for handling salt and other solids contained in the mixture. The system comprises three effect evaporator systems in series. Each effect evaporator system comprises an evaporator, a separator vessel, product pumps, and a solids removal system.

The process utilizes the system to remove salt and other solids as well as excess water leaving a glycol stream that can be reused as a hydrate inhibitor. The process begins by preheating a glycol/brine stream comprising approximately fifty percent (50%) glycol. The stream is then subjected to three evaporation cycles. The first evaporation cycle comprises introducing the preheated stream into a suppressed boiling point evaporator where the stream is heated under a constant pressure. The stream pressure is then dropped to cause a portion of the water contained in the stream to vaporize or flash. The flashing stream is then introduced into a separator vessel where the water vapor is separated from the remaining liquid stream. The water vapor is removed from the separator and condensed. The remaining liquid glycol/brine stream is then pumped from the separator vessel through a solids removal system where precipitated salts and solids are removed. These steps are repeated two additional times. Each time the remaining liquid stream becomes more concentrated with glycol until the finished product is approximately ninety percent (90%) glycol.

19 Claims, 3 Drawing Sheets

PROCESS AND SYSTEM FOR RECOVERING GLYCOL FROM GLYCOL/BRINE STREAMS

CROSS REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates to glycol/water separation. More particularly, the invention relates to a process and a system for recovering glycol from glycol/brine streams produced from oil or natural gas wells.

2. Description of the Related Art

A common problem associated with natural gas production is the formation of hydrates. Hydrates are solid compounds that form as crystals and resemble snow in appearance. They are created by a reaction of natural gas with water, and when formed, they are about 10% hydrocarbon and about 90% water. To prevent plugging of production lines and equipment by hydrates, it is common to inject a hydrate inhibitor into the gas well.

Traditionally, when producing gas offshore, methanol has been used as a hydrate inhibitor because it lowered the freezing point of water vapor and thus prevented hydrate formation in flow lines. The methanol was produced from the well along with the brine and the methanol/brine solution was often disposed of by dumping it into the ocean.

More recently, economic and environmental considerations have forced offshore hydrocarbon producers to consider techniques for recovering hydrate inhibitors from the inhibitor/brine streams. Processes that recover methanol from methanol/brine streams are known to those skilled in the art, however, there are disadvantages to these processes. Particularly, methanol recovery systems generally leave a large portion of the methanol in the brine stream that is lost during disposal. Therefore, the environmental problems associated with disposal of the brine stream continue to exist. Additionally, some methanol is lost along with the vapor phase. Because methanol is lost in the recovery process, additional methanol must be purchased and transported to the offshore platform to make up for the losses.

It has been known to use glycol as a hydrate inhibitor for natural gas streams containing fresh water vapor. Glycol recovery systems are also known to those skilled in the art to remove glycol from the glycol/water streams. Generally, these systems are designed to produce glycol/water streams having between about fifty (50%) and about ninety-five (95%) percent glycol.

As shown in FIG. 1, prior art glycol recover systems primarily consisted of a distillation column 10 in which the glycol was concentrated by distilling off the accompanying water. A natural gas stream containing glycol and water was introduced into a series of separator vessels 12 and 14 where the pressure was reduced to flash off the natural gas. The glycol/water stream was then introduced into distillation column 10 where it was heated by reboiler 16, typically a steam reboiler, to drive the water overhead and concentrate the glycol. The recovered glycol stream produced by this process was approximately ninety-nine percent (99%) glycol.

While glycol is an effective hydrate inhibitor for use with natural gas wells, the glycol recovery systems of the prior art are not particularly suited for recovering glycol from glycol/brine solutions produced from the natural gas wells.

One significant problem with the prior art system of FIG. 1 is created by the salt and other solids contained in the glycol/brine streams. Glycol/brine streams produced from natural gas wells typically contain between about forty percent (40%) and about sixty percent (60%) glycol, about sixty percent (60%) and about forty percent (40%) water with about ten percent (10%) to about twenty-five percent (25%) weight percent dissolved salt in the produced water. The distillation process often results in precipitation of the salt that can foul and plug the recovery system.

Additionally, the prior art glycol recovery systems such as shown in FIG. 1 are extremely energy intensive. Distillation column 10 requires a reboiler 16 to provide the heat necessary to drive off the water vapor. The heat duty required by the reboiler 16 is significant, approximately 300 MM BTU's per hour for a nominal 5,000 barrels per day ("BPD") glycol recovery unit.

Thus, the need exists for an environmentally safe and energy efficient process for recovering hydrate inhibitors that are produced from oil or natural gas wells along with a brine stream. Particularly, the need exists for a process that recovers glycol from glycol/brine streams produced from oil or natural gas wells that is less energy intensive than the prior art systems and is not subject to fouling or plugging problems caused by salt and other solids in the stream. Additionally, the need exists for such a glycol recovery system that can be used on offshore production platforms.

SUMMARY OF THE INVENTION

Briefly, the present invention is a process and a system for recovering glycol from a stream of glycol and brine that has been produced from an oil well or a natural gas well. The present invention provides an energy efficient recovery process and system with capability for handling salt and other solids contained in the glycol/brine stream.

The system of the present invention comprises three effect evaporator systems in series. Each effect evaporator system comprises an evaporator, a separator vessel, product pumps, and a solids removal system. Triple effect evaporator systems have been known to those skilled in the art for concentration of other solutions, however, use of such systems to recover glycol from glycol/brine streams is novel. A particularly novel feature of the system of the present invention is the combination of a triple effect evaporator system with solids removal systems. The solids removal systems can be a combination of a hydrocyclone and strainers, a continuous disk centrifuge, or other solids removal systems known to those skilled in the art.

The process of the present invention is a novel process which utilizes the triple effect evaporator system of the present invention to remove salt and other solids as well as excess water, leaving a glycol stream that can be reused as a hydrate inhibitor. The process of the present invention begins by preheating a glycol/brine stream comprising approximately fifty percent (50%) glycol. The stream is then subjected to three evaporation cycles.

The first evaporation cycle comprises introducing the preheated stream into a suppressed boiling point evaporator where the stream is heated under a constant pressure. The stream pressure is then dropped to cause a portion of the water contained in the stream to vaporize or flash. The flashing stream is then introduced into a separator vessel where the water vapor is separated from the remaining liquid stream. The water vapor is removed from the separator and condensed. The remaining liquid glycol/brine stream is then pumped from the separator vessel through a solids removal system where precipitated salts and solids are removed.

The above mentioned steps of introducing the stream into an evaporator for heating under pressure, dropping the stream pressure to cause a flash, separating the remaining liquid stream from the vapor stream, condensing the vapor stream, and pumping the remaining liquid stream through a solids removal system to remove salts and other solids are repeated two additional times.

Each time these steps are performed the remaining liquid stream becomes more concentrated with glycol and after the third cycle the finished product is approximately ninety percent (90%) glycol. To maximize the energy efficiency of the process of the present invention, heat energy from the water vapor generated in the third evaporation cycle is used to supply heat for the second evaporation cycle, and the heat energy from the second evaporation cycle is used to heat the first evaporation cycle. Additionally, heat from the finished product glycol stream can be recovered and used during the preheating step.

BRIEF DESCRIPTION OF THE DRAWINGS

A better understanding of the invention can be obtained when detailed description set forth below is reviewed in conjunction with the accompanying drawings, in which.

DETAILED DESCRIPTION OF THE PREFERRED INVENTION

The present invention is a glycol recovery system and process for use on mixtures of glycol and brine produced from a hydrocarbon reservoir during the production of natural gas. While the actual concentration of glycol in the brine may vary depending upon production conditions, process of the present invention is preferably used to recover glycol from streams containing about fifty percent (50%) glycol and about fifty percent (50%) brine. Typically, the stream will contain about thirteen percent (13%) sodium chloride. However, those skilled in the art will recognize that the process and the system of the present invention is equally applicable to glycol/brine streams of differing concentrations. Preferably, however the glycol brine streams are in the range of about twenty-five percent (25%) to about seventy-five percent (75%) glycol.

Additionally, the process and system of the present invention is applicable to different types of glycol used as an hydrate inhibitor including ethylene glycol, di-ethylene glycol, and tri-ethylene glycol. However, the process conditions referred to herein refer to processes for recovering tri-ethylene glycol.

When referring to process conditions herein, preferably the actual process temperature is within 15° F. of the stated process temperature and the actual process pressure is within 10 psig of the stated process pressure. More, preferably, the actual process temperature should be within about 5° F. of the stated processs temperature and the actual process pressure is within about 3 psig of the stated process pressure. Additionally, when referring to vacuum conditions, the actual process pressure is within 30 mm Hg of the stated process pressure.

Figure 2:
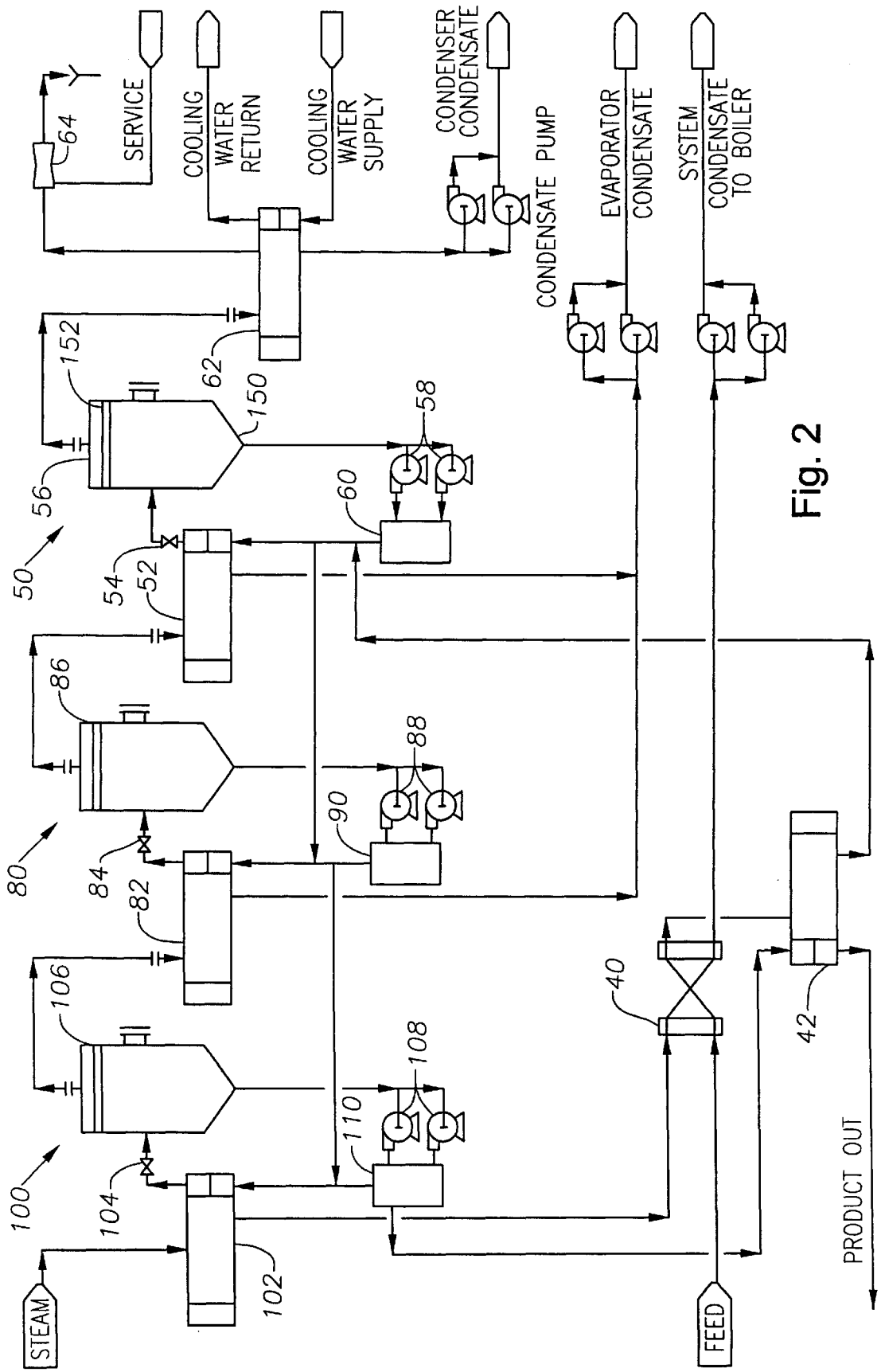
FIG. 2 is a process flow diagram of the process and the system of the present invention.

Referring to FIG. 2, the process of the present invention begins by preheating the glycol/brine feed stream. The degree of preheating is dependent upon temperature of the mixture as it is produced from the well. Generally, this temperature will be approximately 40° F. However, the process of the present invention is equally applicable to mixtures produced at other temperatures. Preferably, the glycol/brine feed stream is preheated in two stages to maximize energy conservation.

A first stage pre-heater 40, in conjunction with a second stage feed pre-heater 42, is used to preheat the feed stream from about 40° F. to about 210° F. Preferably, first stage pre-heater 40 is a plate and frame exchanger such as is commonly known. Steam condensate from a first effect evaporator 102 can be utilized as the heat source for first stage pre-heater 40. First stage pre-heater 40 generally heats the glycol feed stream to about 90° F.

Second stage feed pre-heater 42 further heats the glycol/brine feed stream after it exits first stage pre-heater 40. Preferably, second stage pre-heater 42 is a shell and tube heat exchanger. The final product glycol stream is utilized on the tube side of the exchanger as the heat source for second stage pre-heater 42. This allows recovery of the heat energy from the glycol product stream that would otherwise be wasted by re-injection. Second stage pre-heater 42 heats the glycol/brine feed stream to about 210° F.

As will be recognized, the preheating step is an optional step in the process of the present invention. However, preheating the feed stream does increase the energy efficiency of the process. It will also be recognized that the type and size of exchangers used for preheating can be varied depending upon available stream temperatures and other design considerations commonly understood by those skilled in the art. Additionally, other heat sources available on a production platform may be utilized as alternative heat sources for the preheating step.

After the step of preheating, the glycol/brine feed stream is introduced into a triple effect evaporator system having a first effect evaporator system 100, a second effect evaporator system 80, and a third effect evaporator system 50. The concept of triple effect evaporator systems is well known to those skilled in the art, however, the system of the present invention has adapted the process for use recovering glycol from glycol/brine streams. The system and the process of the present invention are particularly adapted to handle the salt and other solids contained in the glycol/brine streams. Those skilled in the art will recognize that the process and the system of the present invention utilize a reverse feed arrangement. In a reverse feed arrangement the most concentrated solution of glycol/brine is at the highest temperature in first effect evaporator system 100 and the lowest concentrated solution is in the third effect evaporator system 50.

The evaporation process begins by introducing the feed stream into the third effect evaporator 52. Preferably, third effect evaporator 52 is a shell and tube exchanger with titanium or monel tubes and a carbon steel shell. Additionally, evaporator 52 is a suppressed boiling point evaporator such as is known to those skilled in the art. The feed stream is superheated in evaporator 52 to a temperature of approximately 210° F. while the boiling point is suppressed due to maintenance of a back pressure of approximately twenty-five (25) psig by back pressure control valve 54. The back pressure prevents boiling of the glycol/brine feed stream inside evaporator 52 which can result in fouling by the salt or other solids in the stream. Optionally, back pressure can be maintained using valves, piping restrictions, a restricting orifice, elevation, or other means known to those skilled in the art to maintain back pressure.

Next, the pressure of the stream is reduced as the stream is introduced into third effect separator 56. As the pressure is dropped, the superheated feed stream boils and a portion of the water vaporizes inside separator 56. Separator 56 is a vessel capable of withstanding pressures of about 100 psig and also a full vacuum. Preferably, separator 56 has a cone bottom 150 to prevent precipitated salt of solids from accumulating inside separator 56. Separator 56 can be designed with multiple separation trays 152 to prevent glycol from being carried overhead with the water vapor.

Preferably, third effect separator 56 is operated under a vacuum to allow flashing at the lowest temperature possible. Typically, third effect separator 56 will be maintained at approximately 140 mm Hg.

The remaining liquid glycol/brine stream is separated from the water vapor in separator 56. The water vapor exits separator 56 overhead and is condensed in condenser 62. Condenser 62 is preferably a shell and tube exchanger having titanium tubes and a 304 stainless steel shell. Sea water or water from a cooling tower can be used to remove heat in condenser 62.

The condensation of the water vapor creates the vacuum on the separator 56. Additionally, ejector 64 assists in maintenance of a vacuum on separator 56 by handling flow of any non-condensable vapors.

The remaining liquid glycol/brine solution is removed from separator 56 by first effect product pumps 58 and pumped to solids removal system 60 where salt and other solids precipitated solids are removed. Solids removal system 60 can be in the form of the embodiments discussed below or any variety commonly known to those skilled in the art for removing solids from process streams.

The concentration of the glycol/brine stream at this point in the process of the present invention is about 52% glycol and about 48% brine. Preferably, a large portion, about fifty percent (50%) or above, of the glycol/brine stream removed from separator 56 is recycled through evaporator 52 along with the feed stream. Recycling of the glycol/brine increases the heat transfer and decreases fouling as a result of increased velocity through the exchanger tubes. The remaining portion of the glycol/brine stream ("the 52% glycol stream") is introduced into the second effect evaporator system 80 where the above steps are repeated.

The 52% glycol stream is introduced into second effect evaporator 82 where it is heated from approximately 141° F. to approximately 238° F. under a pressure of about 2.6 psig. Second effect evaporator 82 is a suppressed boiling point evaporator of similar design to third effect evaporator 52. Pressure control valve 84 maintains back pressure on the stream as evaporator 82 superheats the stream. The pressure of the stream exiting evaporator 82 is reduced as it is introduced into second effect separator 86. Second effect separator 86 is of similar design as third effect separator 56.

As the pressure is dropped on the stream exiting evaporator 82, it boils and a portion of the water vaporizes inside separator 86. Typically, second effect separator 86 will be maintained at approximately 760 mm Hg or 0 psig.

The remaining liquid glycol/brine stream is separated from the water vapor in separator 86. The water vapor exits separator 86 overhead and is condensed in third effect evaporator 52 where it simultaneously transfers heat to the feed stream. As will be recognized, the recovery of heat from the water vapor increases the energy efficiency of process of the present invention. The remaining liquid in separator 86 is pumped out through second effect product pumps 88 and into solids removal system 90 for removal of precipitated salt and other solids. Solids removal system 90 is of similar construction to solids removal system 60.

The concentration of the glycol/brine stream at this point in the process of the present invention is about 60% glycol and about 40% brine. Preferably, about fifty percent (50%) or above of the glycol/brine stream removed from separator 86 is recycled through evaporator 82 along with the 52% glycol stream. The remaining portion of the glycol/brine stream ("the 60% glycol stream") is introduced into first effect evaporator system 100 where the above steps are repeated.

Figure 1:
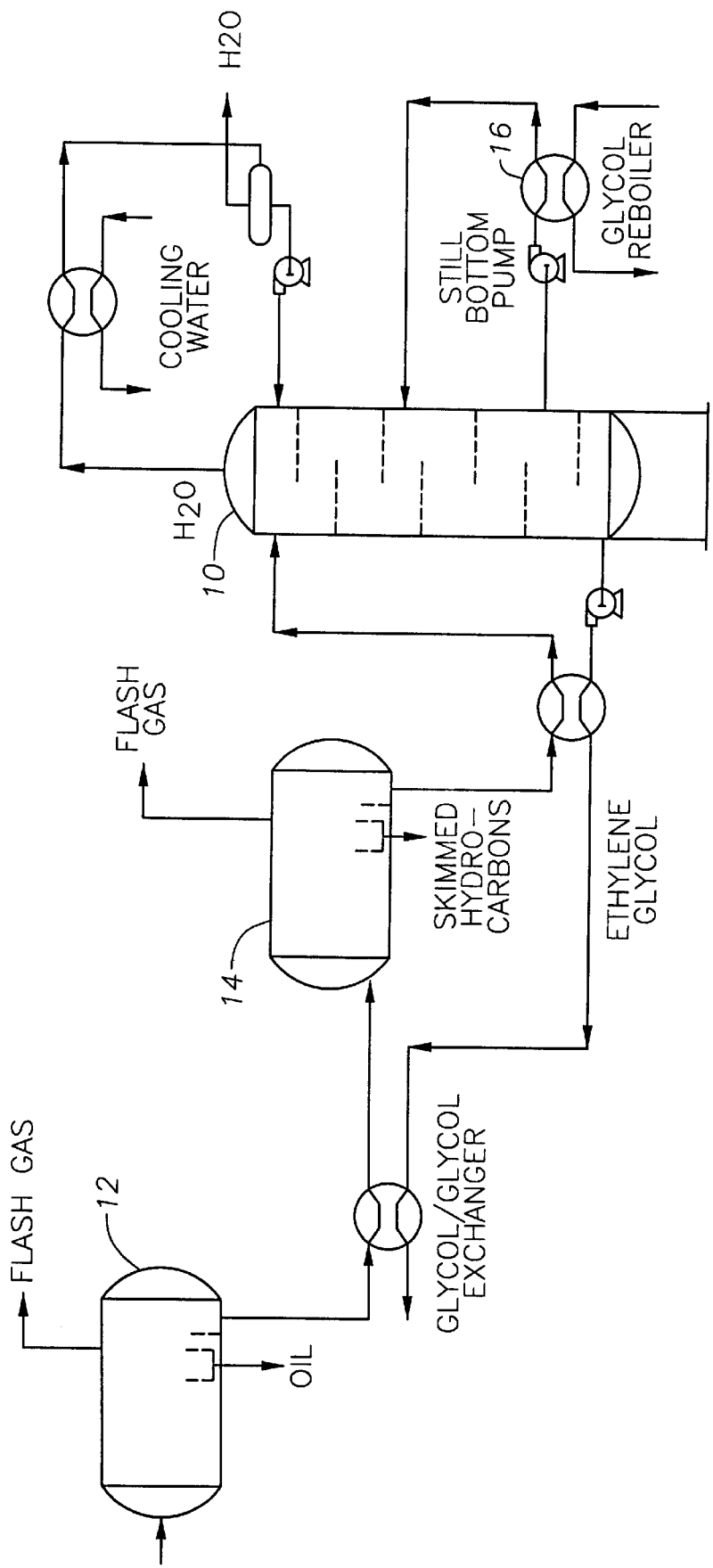
FIG. 1 is a process flow diagram of a prior art system using distillation to remove water from a glycol/water streams.

The 60% glycol stream is introduced into first effect evaporator 102 where it is heated from approximately 229° F. to approximately 344° F. under a pressure of about 30 psig. First effect evaporator 102 is a suppressed boiling point evaporator of similar design to third effect evaporator 52. First effect evaporator 102 is heated by a steam source, preferably 150 psig steam, which can often be supplied by waste heat from other processes. It will be recognized that in the preferred process of the present invention, the steam source to evaporator 102 is the only heat energy added to the process. For an initial feed stream of approximately 10,000 barrels per day, approximately 56 MMBTU/hour of heat energy is required. This compares to approximately 300 MMBTU/hour using the prior art glycol/water concentration process of FIG. 1.

Pressure control valve 104 maintains a back pressure on the stream as evaporator 102 superheats it. The pressure of the stream exiting evaporator 102 is reduced as the stream is introduced into first effect separator 106. First effect separator 106 is of similar design as third effect separator 56. As the pressure is dropped on the stream exiting evaporator 102, it boils and a portion of the water vaporizes inside separator 106. Typically, first effect separator 106 will be maintained at approximately 15 psig.

The liquid stream is separated from the water vapor in separator 106. The water vapor exits separator 106 overhead and is condensed in second effect evaporator 82 where it simultaneously transfers heat to the 60% glycol stream. The condensed water vapors from each of the effect evaporator systems 50, 80, and 100 can be accumulated and disposed of by discharging overboard or by other means.

The remaining liquid in separator 106 is pumped out through first effect product pumps 108 and into solids handling system 110 for removal of precipitated salt and other solids. Solids removal system 110 is of similar construction to solids removal system 60.

The liquid solution after removal of any precipitated salts or solids is the finished product of the process and the system of the present invention. The finished product stream is approximately ninety percent (90%) glycol. As discussed above, the finished product can be cooled in second stage pre-heater 42 where it also serves as a heat source to preheat the feed solution. If desired, a portion of the 90% finished glycol solution stream can be combined with the glycol/brine solution produced from the well to keep the feed steam concentration approximately constant at about fifty percent (50%) glycol and fifty percent (50%) brine.

Figure 3:
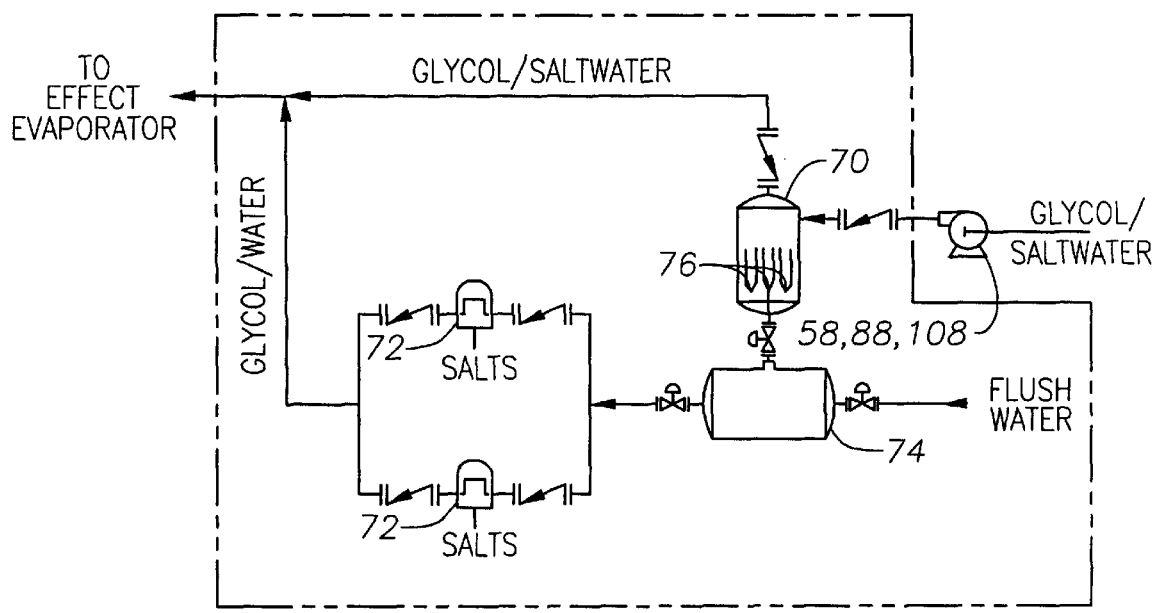
FIG. 3 is a process flow diagram of an embodiment of the solid removal system from the present invention utilizing a hydrocyclone in combination with strainers.

Several embodiments of the solid removal systems 60, 90, and 110 can be utilized in the present invention including various systems for removing solids such as are commonly know to those skilled in the art. As shown in FIG. 3, one embodiment of the solids removal systems 60, 90, and 110 is a combination of a hydrocyclone 70 and strainers 72. Each removal system 60, 90, and 110 is a separate stand alone system, however, a single system will be described below.

Operation and design of hydrocyclones are known to those skilled in the art of solids filtration and removal. The glycol/brine solution is pumped by product pumps 58, 88, and 108 into hydrocyclone 70 where the salts and other solids are separated by centrifugal force. The liquid forms a vortex inside hydrocyclone 70 and salt along with other solids are dropped out an apex 76 at the bottom of hydrocyclone 70 as a slurry. Hydrocyclones acceptable for use with the present invention are available from Baker Hughes Process Systems as part of the Vortoil hydrocyclone separator series (specifically, M-5100-150#).

While hydrocyclone 70 can be used alone to remove solids from the glycol/brine streams, approximately 20% of the liquid stream pumped into hydrocyclone 70 will be lost along with the salt and other solids. To avoid this result, precipitant accumulator 74 and strainers 72 can be used in series with the hydrocyclone to prevent the loss of liquid solution. The solids containing slurry exits hydrocyclone 70 and flows into precipitant accumulator 74 where solids and salt are allowed to settle on the bottom. The glycol solution flows out of accumulator 74 and passes through strainers 72 where it is returned to the glycol/brine streams.

Accumulated salt and solids in precipitate accumulator 74 can then be periodically flushed out with water into strainers 72 where the salt and solids are captured and the flush water is mixed back into the glycol stream. Preferably, precipitant accumulator 74 is a vertical cone bottom vessel that allows removal of accumulated salts. Accumulated salts can be re-mixed with the condensed water from the effect evaporator systems 50, 80, and 100 for disposal.

The hydrocyclone/strainer embodiment of solids removal systems 60, 90, and 110 has the advantages of requiring no moving parts, being less susceptible to plugging, and requires minimal shutdown time for maintenance. Disadvantage of this system include adding additional water back into the process during the accumulator flush and the manual changing and cleaning of strainers 72.

Figure 4:
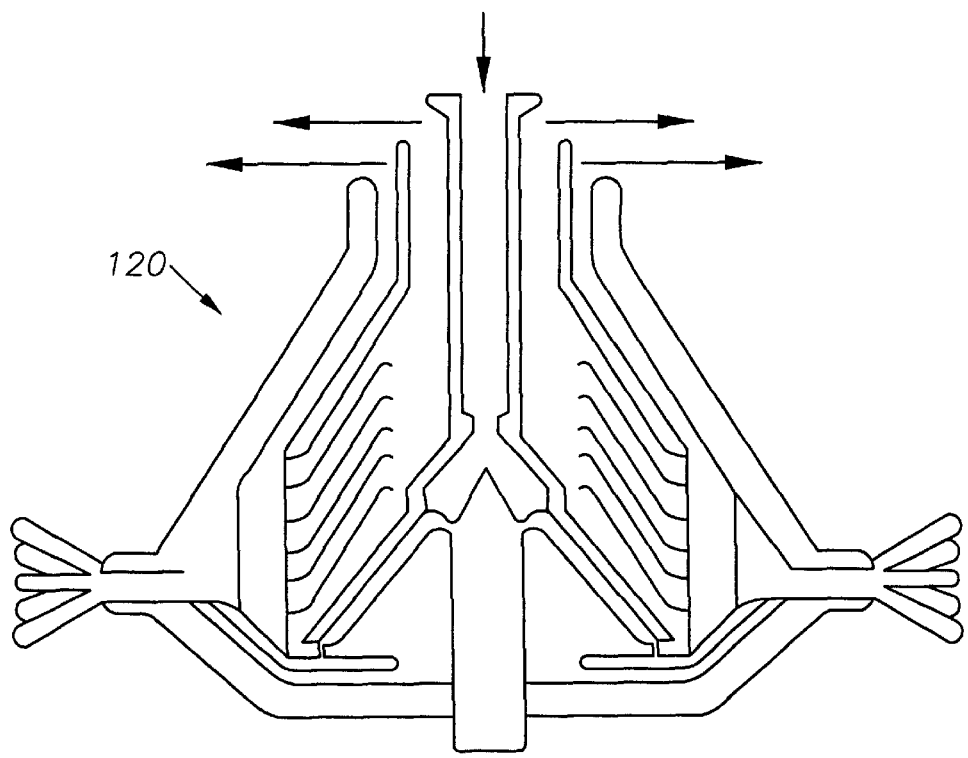
FIG. 4 is an alternative embodiment of the solids removal system from the present invention utilizing a disk centrifuge.

In addition to the embodiment of FIG. 3, solids removal systems 60, 90, and 110 can include continuous nozzle-disk centrifuges 120 (see FIG. 4), acoustic separators, or other means for removing solids as are commonly known in the art. An example of a continuous nozzle-disk centrifuge acceptable for use with the present invention is the Merco model LPH-30-IN.

As can now be recognized, the present invention is a process and a system for recovering glycol from glycol and brine mixtures produced from natural gas wells. The present invention provides an energy efficient recovery system with capability for handling salt and other solids contained in the mixture. Additionally, the present invention is particularly suited for use on offshore production platforms where space and energy conservation are important.

The foregoing disclosure and description of the invention are illustrative and explanatory thereof, and various changes in the details of the illustrated apparatus and construction and method of operation may be made without departing from the spirit in scope of the invention.

What is claimed is:

1. A method for recovering glycol from a mixture of glycol and water, comprising the steps of:
   heating the glycol and water mixture under pressure;
   reducing the pressure on the glycol and water mixture to initiate a flash and vaporize a portion of water from the mixture;
   separating the vaporized water from the remaining glycol and water mixture;
   heating the remaining glycol and water mixture under pressure;
   reducing the pressure on the remaining glycol and water mixture to initiate a flash and vaporize a portion of the water from the remaining mixture;
   separating the vaporized water from the more concentrated glycol and water mixture;
   heating the more concentrated glycol and water mixture under pressure;
   reducing the pressure on the more concentrated glycol and water mixture to initiate a flash and vaporize a portion of water from the more concentrated mixture; and
   separating the vaporized water from the concentrated glycol stream;
   wherein the vaporized water from the third separation step provides the heat for the second heating step and the vaporized water from the second separations step provides the heat for the first heating step.

2. The method of claim 1 further comprising the step of removing precipitated solids from the remaining glycol and water mixture after the first separation step and before the first heating step.

3. The method of claim 1 further comprising the step of removing precipitated solids from the more concentrated glycol and water mixture after the second separation step and before the second heating step.

4. The method of claim 1 further comprising the step of removing precipitated solids from the concentrated glycol stream after the third separation step.

5. The method of claim 1 further comprising the step of preheating the glycol and water mixture before the first heating step.

6. A method for recovering glycol from a mixture of glycol and brine, comprising the steps of:
   heating the glycol and brine mixture under pressure;
   reducing the pressure on the glycol and brine mixture to initiate a flash and vaporize a portion of water from the mixture;
   separating the vaporized water from the remaining glycol and brine mixture;
   removing precipitated solids from the remaining glycol and brine mixture
   heating the remaining glycol and brine mixture under pressure;
   reducing the pressure on the remaining glycol and brine mixture to initiate a flash and vaporize a portion of the water from the remaining mixture;
   separating the vaporized water from the more concentrated glycol and brine mixture;
   removing precipitated solids from the more concentrated glycol and brine mixture;
   heating the more concentrated glycol and brine mixture under pressure;
   reducing the pressure on the more concentrated glycol and brine mixture to initiate a flash and vaporize a portion of water from the more concentrated mixture; and separating the vaporized water from the concentrated glycol stream;

removing precipitated solids from the concentrated glycol stream;

wherein the vaporized water from the third separation step provides the heat for the second heating step and the vaporized water from the second separation step provides the heat for the first heating step.

7. The method of claim 6 further comprising the step of preheating the glycol and brine mixture before the first heating step.

8. The method of claim 6 wherein the glycol and brine mixture of the first heating step comprises between about twenty five and about seventy five percent by weight glycol.

9. The method of claim 6 wherein the brine portion of the mixture comprises between about thirteen percent and about twenty five percent by weight salt.

10. The method of claim 6 wherein the first heating step comprises heating the glycol and brine mixture to between about 205° F. and about 210° F. at a pressure of between about 22 psig and about 28 psig.

11. The method of claim 6 wherein the first pressure reducing step comprises reducing the pressure to less that 760 mm Hg.

12. The method of claim 6 wherein the first pressure reducing step comprises reducing the pressure to between about 110 mm Hg and about 170 mm Hg.

13. The method of claim 6 wherein the second heating step comprises heating the remaining glycol and brine mixture to between about 233° F. and about 242° F. at a pressure between about 0 psig to about 6 psig.

14. The method of claim 6 wherein the second pressure reducing step comprises reducing the pressure to between about 0.6 psig and about 730 mm Hg.

15. The method of claim 6 wherein the third heating step comprises heating the more concentrated glycol and brine mixture to between about 339° F. and about 349° F. at a pressure of between about 27 psig and about 33 psig.

16. The method of claim 6 wherein the third pressure reducing step comprises reducing the pressure to between about 12 psig and about 18 psig.

17. The method of claim 6 further comprising the step of recycling a portion of the remaining glycol and brine mixture from the first solids removing step to the first heating step.

18. The method of claim 6 further comprising the step of recycling a portion of the more concentrated glycol and brine mixture from the second solids removing step to the second heating step.

19. The method of claim 6 further comprising the step of recycling a portion of the concentrated glycol stream from the third solid removing step to the third heating step.

* * * * *